(12) United States Patent
Apostolos et al.

(10) Patent No.: US 8,773,127 B2
(45) Date of Patent: *Jul. 8, 2014

(54) TRANSMISSION LINE ARRAY FOR EXPLOSIVE DETECTION USING NUCLEAR QUADRUPOLE RESONANCE

(75) Inventors: John T. Apostolos, Lyndeborough, NH (US); Paul A. Zank, Brookline, NH (US)

(73) Assignee: R.A. Miller Industries, Inc., Grand Haven, MI (US)

( * ) Notice: Subject to any disclaimer, the term of this patent is extended or adjusted under 35 U.S.C. 154(b) by 687 days.

This patent is subject to a terminal disclaimer.

(21) Appl. No.: 12/957,859

(22) Filed: Dec. 1, 2010

(65) Prior Publication Data

US 2012/0161761 A1    Jun. 28, 2012

Related U.S. Application Data

(60) Provisional application No. 61/299,663, filed on Jan. 29, 2010.

(51) Int. Cl.
*G01V 3/00* (2006.01)
*G01R 33/20* (2006.01)
*G01R 33/3815* (2006.01)

(52) U.S. Cl.
USPC ............. 324/307; 324/309; 324/318; 702/23

(58) Field of Classification Search
CPC ................ G01R 33/4828–33/4836; G01R 33/561–33/5615
USPC ........ 324/300–322; 702/22–23; 600/407–464
See application file for complete search history.

(56) References Cited

U.S. PATENT DOCUMENTS

| 4,513,292 | A | 4/1985 | Bowman | |
|---|---|---|---|---|
| 5,206,592 | A * | 4/1993 | Buess et al. | 324/307 |
| 5,608,321 | A | 3/1997 | Garroway et al. | |
| 6,046,586 | A | 4/2000 | Rinard | |
| 6,104,190 | A * | 8/2000 | Buess et al. | 324/300 |
| 6,822,444 | B2 * | 11/2004 | Lai | 324/300 |
| 6,900,633 | B2 * | 5/2005 | Sauer et al. | 324/307 |
| 7,119,682 | B1 | 10/2006 | Fisher | |
| 7,170,288 | B2 | 1/2007 | Fullerton | |
| 7,352,180 | B2 | 4/2008 | Manneschi | |
| 7,365,536 | B2 | 4/2008 | Crowley et al. | |

(Continued)

OTHER PUBLICATIONS

U.S. Appl. No. 12/957,820, filed Dec. 1, 2010; Long Distance Explosive Detection Using Nuclear Quadrupole Resonance and One or More Monopoles.

(Continued)

*Primary Examiner* — Jermele M Hollington
*Assistant Examiner* — Emily Chan
(74) *Attorney, Agent, or Firm* — McGarry Bair PC

(57) ABSTRACT

A transmission line array is used for explosive/contraband detection using nuclear quadrupole resonance in which the array is driven in-phase with synchrony frequency-swept signals. Each of the balanced transmission lines is fed with a low power swept frequency source and stimulated emissions are picked out with a directional coupler. Location is provided using a cross grid array or a phase detector is used for each balanced line, with phase determining the distance to the sensed substance.

10 Claims, 11 Drawing Sheets

(56) References Cited

U.S. PATENT DOCUMENTS

| | | |
|---|---|---|
| 7,397,239 B2 | 7/2008 | Crowley et al. |
| 7,417,440 B2 | 8/2008 | Peschmann et al. |
| 7,511,496 B2 | 3/2009 | Schiano |
| 7,595,638 B2 | 9/2009 | Crowley |
| 7,768,262 B2 | 8/2010 | Schiano |
| 7,888,646 B2 | 2/2011 | Breit et al. |
| 2004/0222790 A1 | 11/2004 | Karmi et al. |
| 2005/0241639 A1 | 11/2005 | Zilberg |
| 2006/0012371 A1 | 1/2006 | Laubacher et al. |
| 2006/0122484 A1 | 6/2006 | Itozaki et al. |
| 2006/0132127 A1 | 6/2006 | Fullerton |
| 2008/0036462 A1* | 2/2008 | Schiano ............... 324/318 |
| 2008/0309339 A1 | 12/2008 | Chisholm et al. |
| 2009/0153346 A1 | 6/2009 | Crowley et al. |
| 2010/0212401 A1 | 8/2010 | Crowley et al. |

OTHER PUBLICATIONS

U.S. Appl. No. 12/957,843, filed Dec. 1, 2010; Method and Apparatus for Sensing the Presence of Explosives, Contraband and Other Molecules Using Nuclear Quadrupole Resonance.

U.S. Appl. No. 12/957,859, filed Dec. 1, 2010; Transmission Line Array for Explosive Detection Using Nuclear Quadrupole Resonance.

U.S. Appl. No. 12/957,893, filed Dec. 1, 2010; Long Range Detection of Explosives or Contraband Using Nuclear Quadrupole Resonance.

U.S. Appl. No. 12/957,919, filed Dec. 1, 2010; Shipping Container Explosives and Contraband Detection System Using Nuclear Quadrupole Resonance.

U.S. Appl. No. 12/957,948, filed Dec. 1, 2010; Method and System for the Detection and Identification of Explosives and/or Contraband.

\* cited by examiner

TRANSMISSION LINE ARRAY FOR EXPLOSIVE DETECTION USING NUCLEAR QUADRUPOLE RESONANCE

RELATED APPLICATIONS

This application claims rights under 35 USC §119(e) from U.S. Application Ser. No. 61/299,663 filed Jan. 29, 2010, the contents of which are incorporated herein by reference.

FIELD OF THE INVENTION

This invention relates to the use of nuclear quadrupole resonance for the detection of molecules and more particularly to the use of an array of balanced transmission lines to, detect molecules such as explosives, narcotics and other molecules of interest over wide areas.

BACKGROUND OF THE INVENTION

In the early 1900s, not long after Einstein published his equations on thermal equilibrium, individuals realized that there were likely to be resonances at very low frequencies for atoms and molecules and that these resonances would occur because if one emits a photon of exactly the correct frequency, the material will absorb this photon, store it for some amount of time and then get rid of the absorbed energy. It is has been found that in nature the molecules which absorb such energy always fall to a lower energy state.

One of the ways for the material to emit energy is through spontaneous emission where a photon of exactly the same energy that is impinging on the material is thrown off in a random direction at random times.

The second way of getting rid of the energy absorbed by the material is through process of stimulated emission in which a photon arrives at exactly the appropriate energy, gets near the molecule, stimulates the molecule and when the molecule drops to the lower energy state it emits a photon that is exactly in phase with the original photon.

The energy that is thrown off either in spontaneous emission or stimulated emission results in an exceedingly narrow spectral line. In fact the line is generally considered to be a single line that exists at a given wavelength or frequency. It is noted that the material only has one choice assuming that the material is pumped at its lowest energy state, raising the energy within the molecule such that the only way that it can release its energy is to emit a photon of that exact energy.

Nuclear quadrupole resonance has been utilized in the past to detect the presence of specific molecules, including explosives. Explosives generally involve the use of nitrogen or nitrogen bonded with other elements. When nuclear quadrupole resonance was utilized in the past, it was used to detect the presence of molecules due to the molecular elements that are bonded together such that the molecules absorb energy at for instance as many as eight different energy levels or spectral lines. It turns out that at least three of the energy levels tend to be prominent, although in some materials there are upwards of all eight energy levels for one bond. If one has many bonds there may be many dozens of spectral lines. In order to detect the presence of a molecule one usually is looking to pump energy right at the top of one of the spectral lines and look for energy coming back at the same frequency.

As discussed in co-pending patent application by Paul A. Zank and John T. Apostolos, entitled Method and Apparatus For Sensing The Presence Of Explosives, Contraband and Other Molecules Using Nuclear Quadrupole Resonance, BAEP-1277, filed on even date herewith and incorporated herein by reference, as part of the subject invention, it has been found that the spectral lines of interest especially for explosives are in the 100 KHz to 10 MHz range. A particularly interesting explosive is called RDX which has a spectral line in the 3 to 4 MHz range, as does sodium nitrate.

However if one is seeking to detect stimulated or emission or spontaneous emission at 3 MHz, the wavelength of the returns is incredibly long, in some cases corresponding to the size of a building. Moreover, the photons that are emitted in either spontaneous or stimulated emission represent very little energy. For instance, a red photon carries an energy of about 3.5 electron volts, with detectable radiation being one or two millionths of 3.5 electron volts. The result is that photons emitted from the molecules are virtually undetectable. One of the reasons is that in order to detect single photons one is faced with, thermal background that overwhelms the detection process. In order to achieve any type of result, one pumps large numbers of photons into the target material such that for every milliwatt second an extraordinary number of photons are involved.

If the photons are at the appropriate frequency they are absorbed and only when the frequency exactly corresponds to a resonance line does the molecule start absorbing the photons. Thus it is quite important that the frequency source utilized in the nuclear quadrupole resonance measurements be extremely precise and stable.

If one performs a frequency sweep, the emission that comes back is on the order of 1% of the energy that impinges on the molecule.

It is noted that prior nuclear quadrupole resonance techniques can be likened to looking into a headlight to find a 1% response.

As a result, a pulsed coil prior art nuclear quadrupole resonance detection of molecules requires upwards of 100 kilowatts of energy coupled to a very high Q tuned coil having for instance a Q of 80 or better. If there is any offset in terms of the frequency of the incident radiation or if the coil tuning was not precise, then any emissions from the molecule will be lost in the clutter.

First and foremost in the prior art pulsed coil nuclear quadrupole resonance techniques, it was only with difficulty that one could in fact detect any response. One of the reasons is because the coil exhibits a large dwell time after which one looked for a response.

If one did not wait, the incoming radiation would swamp the detectable results. In order to eliminate this problem, those in the past used a pulsed source and then waited for a response after the trailing edge of the pulse. Prior systems thus pumped pulsed energy into a coil with the target material at the center of the coil. Thereafter the material would absorb energy and then the prior systems would listen for the spontaneous decay.

The problem with spontaneous decay is that at thermal equilibrium a spontaneous photon happens only once for every two million stimulated photons. Thus, in terms of detecting spontaneous decay, one is at an extremely difficult power disadvantage. Secondly, the spontaneous decay might happen over several tens of milliseconds which means that the instantaneous power levels at any point in time are very low. For spontaneous decay using a pulsed coil nuclear quadrupole resonance, the problem is that one is working with very few photons and further they are stretched out over time. This means that one has to use huge amounts of power to overcome these problems, often in the nature of kilowatts of energy. Moreover, because one is looking at very low signal strength the coil is made with a very high Q. This means that the coil couples well with the environment, that in turn means that the coil picks up a great deal of background noise.

Pulsed coil nuclear quadrupole resonance detection systems have been marginally cost effective and their power density has exceeded human safe limits.

More specifically, taking RDX as an example, the bandwidth of the RDX resonance is about 400 hertz. This means that the associated decay time or relaxation time is on the order of 2.5 milliseconds. If one were to sweep the frequency through the resonance as one approaches the resonant frequency, what happens is that one excites the nucleus of the nitrogen atom. When the nucleuses are excited they go into an upper state and then as one sweeps by the frequency there is a population inversion in these nuclei at which time they start to decay.

If one utilizes a long CW pulse what would happen is that one would see a periodicity of absorption and emission. When the CW pulse is turned on, the molecule goes into the excited state but then relaxes through stimulated emission. What would happen utilizing a CW signal is that one would see a series of absorptions and emissions that would occur every 2.5 milliseconds.

For RDX, assuming a pulsed coil system, one must use a pulse width of about half a millisecond because the pulse has to decay down fast enough so that the spontaneous emission can be observed.

Thus in the past a relatively short pulse of CW energy was used to enable listening for the response. However, in order to be able to detect the response at all, a very high Q coil was required. High Q coils have an excessive relaxation time. As a result, in order to provide for the ability to listen when driving a very high Q coil at half a millisecond one has to have other circuitry to quench the coil as fast as possible so as to be able to listen to the return, typically in terms of a little hiss that comes off after irradiation with the pulse.

Thus, in the prior systems one had to have exceedingly large kilowatt sources of 3 MHz energy in order to obtain enough of a response, and then had to pulse the source so as to be able to stop it and quench it in time to be able to detect the minuscule response that would occur.

Having the high Q coil further was complicated by the fact that one could not frequency sweep a sample because the high Q coil resonates at only one frequency.

This for instance precludes the ability to distinguish between the detection of multiple spectral lines to be able to distinguish the spectral response of the target molecules from the spectral responses from uninteresting molecules.

Also, when using a high Q coil one has to use an exceedingly large amount of shielding to make the system safe for use around people, as well as having to actively quench the coil.

Moreover, when pumping 1 kilowatt into a coil, the presence of the system is very easy to detect. Thus, terrorists could avoid screening knowing that such a detection system was in operation.

Note that the pulsed coil system detects spontaneous not stimulated emissions. Spontaneous emissions are not coherent and one obtains the square root of the power coming back.

Thus, in the past it has been virtually impossible to provide a workable system that would reliably and safely detect dangerous amounts of explosive material hidden on a human

SUMMARY OF INVENTION

According to the invention, a system is provided for detecting substances utilizing nuclear quadrupole resonance across an extended area. The system includes an array of balanced transmission lines located side by side in an area. Each balanced transmission line is terminated with a load equal to the impedance of the transmission line so that the transmission line is balanced and effectively has a Q of zero. The system also includes a frequency source for simultaneously driving each of the transmission lines with a transmission signal having a frequency equal to that of a spectral line of a substance located in the area. A series of detectors, one each per balanced transmission line, is configured to detect received signals from the balanced transmission lines indicative of stimulated emissions caused by nuclear quadrupole resonance of the substance near the balanced transmission lines. And a processor is coupled to the detectors for processing any detected received signals to indicate the presence of the substance in the area.

BRIEF DESCRIPTION OF THE DRAWINGS

These and other features of the subject invention will be better understood in connection with the Detailed Description, in conjunction with the Drawings, of which.

DETAILED DESCRIPTION

Figure 1:
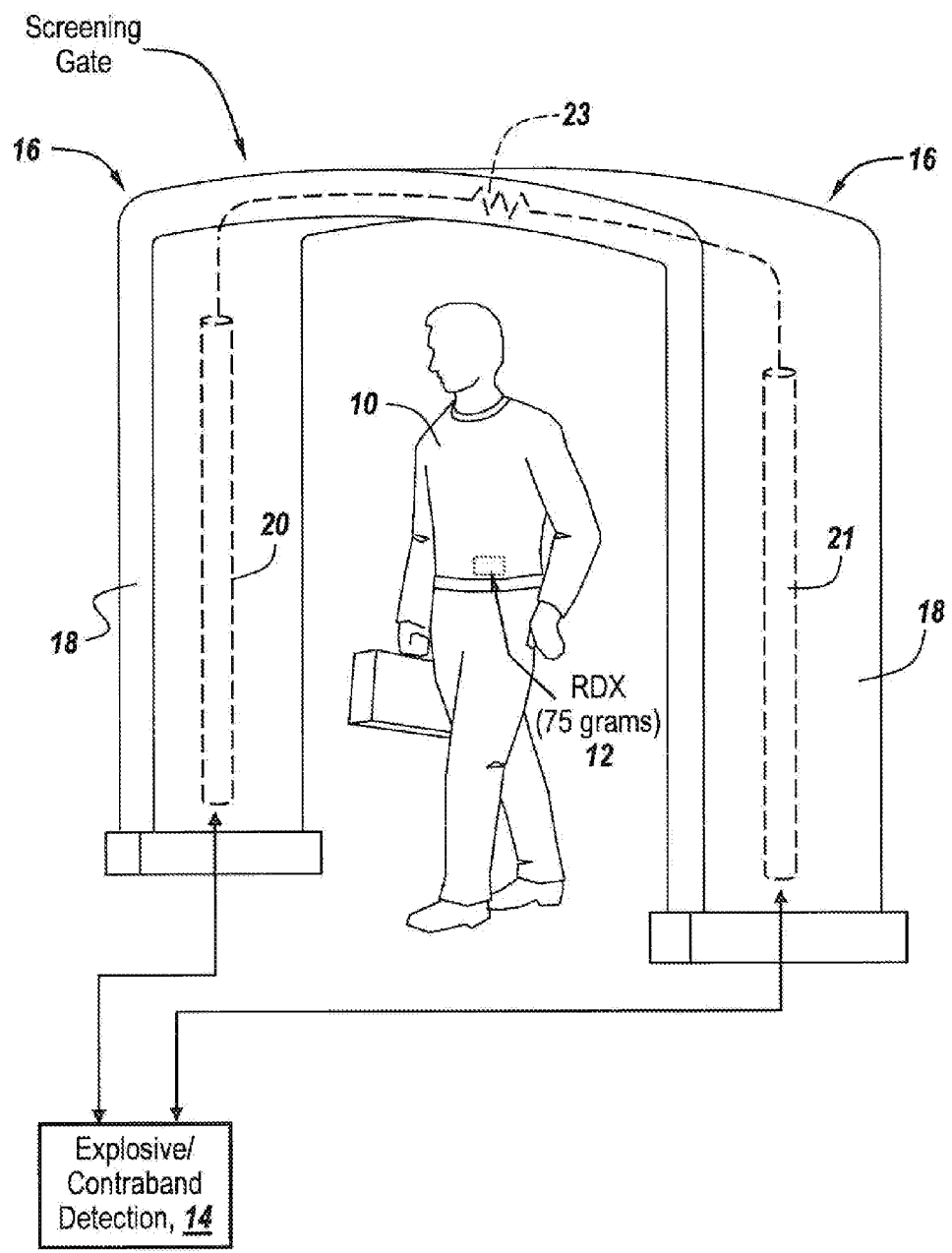
FIG. 1 is a diagrammatic illustration of the detection of an explosive hidden on an individual as the individual walks through a balanced transmission line coupled to an explosive/contraband detection unit that utilizes nuclear quadrupole resonance in which, in one embodiment, RDX spectral lines are detected to ascertain the presence of an explosive.

By way of further background, for the basic NQR system a low power swept frequency source is used in combination with a probe in the form of a terminated balanced transmission line in which molecules including explosives, narcotics and the like that are located between the transmission line elements are detected. In this basic system the result of the absorption of the milliwatt/watt energy is picked off with a directional coupler or circulator so as to eliminate the transmitted energy from swamping the received energy. What is seen is the 1% stimulated emission coherent result that is exactly in-phase with the transmitted signal. It is the coherent in-phase relationship that permits integrating the weak signals into a detectable result.

As a result of utilizing the directional coupler the transmitted signal is rejected. Moreover, the utilization of a balanced transmission line essentially has a zero Q, thus eliminating the background noise associated with the high Q coils. Moreover, since the transmission line is not resonant at any one frequency, a sample can be frequency swept or simultaneously irradiated with signals at multiple frequencies. Additionally, there is no frequency limit to the sweep frequency since there are no tuned circuits involved.

In one embodiment of the basic system, the energy is step wise swept so as to be able to correlate the result with spectral lines of a known molecule while being able to reject returns from molecules having other spectral lines.

It has been found for explosives such as TNT, RDX and PETN and other molecules of interest that sweeping between 100 KHz and 10 MHz is enough of a sweep to discriminate against non-target materials. For instance, while one might be looking for the spectral lines associated with RDX, one would also like to be able to ignore the spectral lines of for other materials, or for that matter glycine which is present in a great many biologic materials.

The basic system is typically operated at between 200 milliwatts up to 10 watts, making the system much safer than the high power kilowatt pulsed coil nuclear quadrupole resonance systems. Moreover, quenching is unnecessary.

For robust detection of the stimulated emission, more than one spectral line can be considered as an indicator of the molecule. For instance, for RDX one might wish to look at two or three of the RDX spectral lines. If it turns out that glycine is present, and if in fact one of the RDX spectral lines share a spectral line with the glycine, then one could ignore the overlapping spectral line.

While scanning network analyzers can be utilized as frequency sources for the subject invention, due to the fact that the transmission line does not discriminate from one frequency to the next, it is possible to connect multiple frequency sources in parallel to feed the transmission line resulting in simultaneous evaluation of several frequencies.

It is also possible to use a pseudo-random number code pattern so that the system would be difficult to jam. Moreover, the low power system is hard to detect, obscuring the fact that any scanning is going on at all.

In one embodiment of the basic system while one could scan from 100 KHz to 10 MHz, this type of scanning procedure wastes a large amount of time and is not necessarily beneficial. If one is only looking for specific resonance lines, the scanning can be scheduled to appropriately frequency hop, thus dramatically reducing scanning time.

Note in the subject system that no single detection of a spectral line is used to declare the presence of the target material. Rather, the system desirably requires multiple hits in order to declare the presence of the target material.

It is also noted that the subject system looks at the stimulated emissions, as opposed to the spontaneous emissions, primarily because the spontaneous emissions are perhaps one two millionth of the power of the stimulated emissions. This is important because, as mentioned above, in determining the presence of a target molecule, one is seeing only 1% of the incident energy being returned.

Further, RDX resonances have a bandwidth of approximately 400 hertz, which as mentioned above, results in a decay time or relaxation time of about 2.5 milliseconds. Assuming a stepped sweep approach, the nucleus of the atoms making up the molecules are excited and when they go into the upper state, there is a population inversion in these nuclei, with the stimulated emission occurring immediately thereafter. Note that the stimulated atoms that have been inverted relax coherently such that there is a coherent response back to the probe. Because of the 2.5 millisecond relation time stepped sweeps would have to be adjusted accordingly.

Since there is no coil involved, one does not have to use quenching and since one uses a directional coupler to ignore the transmitted signal, one does not have to stop and listen in order to get adequate readings.

Moreover, in one embodiment of the subject invention, a cancellation algorithm is utilized in which the transmission line is observed without a sample between the transmission line elements during a calibration sweep. Thereafter, any material that is between the transmission line elements has results that are subtracted from the calibration sweep results. Thus, if there are any peculiarities in the analyzer or transmission lines, these peculiarities are subtracted out. As a result, steady state noise is nulled out.

The reason for the use of the transmission line is that it focuses all the energy between the two balanced leads or elements. Because a balanced transmission line is the world's worst antenna by design it does not leak energy to the environment, unlike a coil. Concomitantly, the transmission line does not receive interference from the environment, making the subject system an extremely quiet system.

The basic system is implementable in a number of different forms such as providing two spaced apart transmission line elements to either side of a gate or portal through which an individual is to pass. Such a portal may be an airport security checkpoint. Moreover, two pieces of copper pipe or copper tape may be placed on opposing walls down a corridor to form the transmission line, or the balanced transmission lines can be placed on a road to detect the passage of target material between the transmission line elements. Additionally, the transmission line could for instance be configured as opposed guard rails.

It will be appreciated that the basic system, by avoiding the high Q coil, also avoids the large amount of shielding necessary for public safety or the safety of those operating the equipment. Also, as mentioned above, there is no need to actively quench any part of the probe in order to be able to listen to the relatively small returns from the irradiated sample.

Rather than having to run a kilowatt into a coil, in the subject invention successes have been reported at a 200 milliwatt level with excellent signal to noise ratios. Thus, there is the ability to operate at a 30 dB lower power levels than a pulsed coil. This means that the entire system can be run at low power. The result is that the basic system does not interfere with magnetic media or people's safety and is very hard to detect any distance away from the test site. Thus, even standing a few feet beside the balanced transmission line one is not able to detect it. As a result, a person would not know that he or she is being monitored. Also, if a pseudo-random hopping schedule is utilized, detection of the presence of such a system is virtually impossible.

As will be appreciated, the conductors for the transmission lines could be for instance as large as a two inch pipe, or could in fact be flat transmission line elements. It is also noted that the termination resistance is equal to the impedance of the transmission line. In one embodiment, the space between the elements is about 2.5 to 3 feet, such that one could conveniently paint conductive stripes on opposing sides of a corridor, with the impedance being controlled by how tall the stripes are and how far apart the stripes are. For a corridor-sized installation one might have a conductive stripe on either side of the corridor that is 11 feet long and about a foot tall. Also with larger areas one needs more power to create the flux density required. Thus if one considers a 12 foot long probe, this requires about 36 times as much power as a miniature probe. It is the power density (watts/meter^2) that remains constant.

Regardless, one can obtain adequate results in a corridor type situation with between 7 and 10 watts of power into the probe.

The amount of power required is dependant on how much material one is trying to detect and also the flux density that one is trying to excite it with, as well as how much integration time is available.

Small amounts of explosives can be carried on the person in the persons clothing, swallowed, or can even be surgically implanted, which would be virtually undetectable through a physical examination of the person and also through standard X-ray techniques. Thus for the creative or diligent terrorist, it may be of interest to provide pockets of the explosive within the body of the individual that could not be readily detected by present techniques.

It is noted that the maximum flux density given two spaced apart conductors is on a line between the two conductors, with the minimum being outside the transmission line. As one proceeds to the edge of the conductors, one obtains more flux density. However, the flux density does not very significantly in a direction normal to the plane between the two transmission line elements so it is possible to get reasonable coverage for a human sized object or even a truck sized object above the transmission line. Note that the transmission line impedance can typically be between 100 and 1,000 ohms which is not critical. The critical component is the flux density, with the critical flux density being approximately 1 watt per meter$^2$.

With a flux density of less than 1 watt per meter$^2$, the signal-to-noise ratio is less for the same integration time. If the flux density is greater than 1 watt per meter$^2$, then the signal-to-noise ratio is improved because of the coherent signal. The result of the coherency is that the signal-to-noise ratio improves linearly with how much integration time is utilized.

Integration time refers to the collection of the results of multiple stimulated emissions over time. As a general rule, one has to dwell on the target material for whatever is the inverse of the particular bandwidth involved. Bandwidths in the subject case are on the order of a 100 to 500 hertz which results in dwell times of between 1 and 5 milliseconds.

Of course, as mentioned above, one need not frequency hop in 1 to 5 millisecond intervals because there is no reason why one cannot monitor multiple lines simultaneously or even feed the lines with parallel-outputted frequency generators. In short if one were using three signal generators coupled to the same transmission line, one could sense three different spectral lines simultaneously.

Since the subject system can sample multiple frequencies simultaneously this is considerably different from the pulsed coil nuclear quadrupole resonance systems that tend to tune a coil for a specific frequency because of the need for the high Q. Thus, in the subject system one can track the results over the entire bandwidth utilizing the same balanced transmission line probe.

As a result, the subject system is capable of detecting an entire class of explosives, whether they are people-born or vehicle-born. Moreover, the subject system may detect contraband such as narcotics, with many narcotics having very specific nuclear quadrupole resonance signatures. This includes cocaine and heroin.

It will be appreciated that for some complex organics the spectral lines tend to be larger, such as those associated with glycine. Glycine, even in its usual 5% concentration for dietary supplements, for instance, can be distinguished by recognizing the glycine spectra and subtracting out the nuclear quadrupole resonance signature. As a result, if it turns out that one of the spectral lines happens to be right on top of the molecule of interest, the subject system provides way to discriminate against the non-target molecules.

Another application is to be able to detect explosives in shipping containers. In such cases one has an incredibly long integration time available, for instance weeks during which the inspection can take place.

Another different application for the subject technique is in the production of molecular compounds. Explosives for instance have a certain composition which involves a very specific ratio of the molecular components. It has been found that the subject technique can be used to verify the specific percentage ratio of the components in the test sample, so that one can non-destructively inspect materials during production without damaging it.

It has been found that the detected spectral lines are one-to-one correlatable with the ratio of the molecular constituents in a compound so that the measurements are a very accurate prediction of the actual ratio of the elements in the compound.

Moreover, it has been found that the stability of the frequency source and its accuracy is important with respect to the stability of the oscillators involved, with the aforementioned cancellation requiring suitably stable oscillators.

With suitably stabilized oscillators in the form of for instance multiple network analyzers, one can digitally synthesize multiple frequencies simultaneously. Fast-Fourier transforms are then used to sort out the frequencies. In this case one piece of hardware can generate multiple frequencies simultaneously. This cuts down the time that the specimen has to be between the elements of the balanced transmission line, thus for instance to be able to detect somebody who is running with explosives.

For stepped frequency sweeps, one can allocate 5 milliseconds per frequency. If one is analyzing 10 spectral lines then one is doing so in 50 milliseconds. However, the problem is that there may be 40 or 50 different prominent explosives, all with different spectral lines, and hundreds of compounds that have spectral lines in the same region. Thus instead of processing 10 spectral lines, one might have to process 1,000 spectral lines. At 50 hertz, this corresponds to a dwell time of 5 seconds and necessitates synthesizing all frequencies of interest simultaneously.

In summary, in the basic system stimulated emissions due to nuclear quadropole resonance are detected utilizing an array of terminated balanced transmission lines and directional couplers, thus to detect explosives, contraband, narcotics and the like that exist between the transmission line elements, as well as to locate detected substances. In one embodiment, a stepped frequency generator is utilized to provide a scan between 100 KHz and 10 MHz. In another embodiment, parallel frequency sources are in-phase coupled to the balanced transmission lines, either embodiment permitting correlation with expected spectral lines, with the frequency sources being low power so as to not create a safety hazard and so as not to interfere with radiation sensitive devices such as film or electronic circuits that are in the vicinity of the balanced transmission lines.

The NQR System

Figure 11:
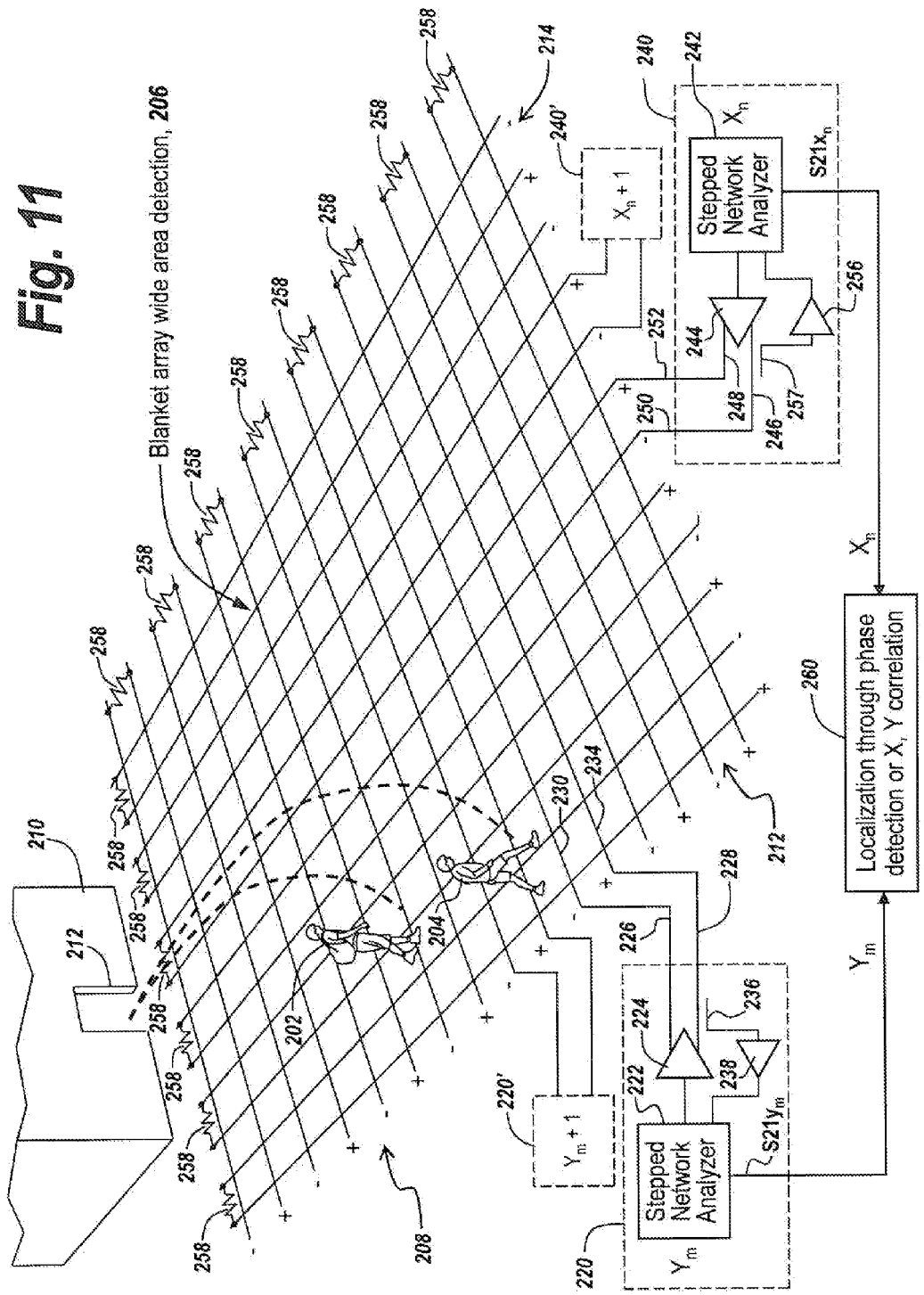
FIG. 11 is a diagrammatic illustration of a wide area array grid of terminated balanced transmission lines for detection of a sensed substance as well as location at a cross point; and, FIG. 12 is a diagrammatic illustration of a balanced transmission line methodology for feeding the transmission lines in parallel and for detecting the position of a sensed substance either at or between balanced transmission lines.
Figure 12:
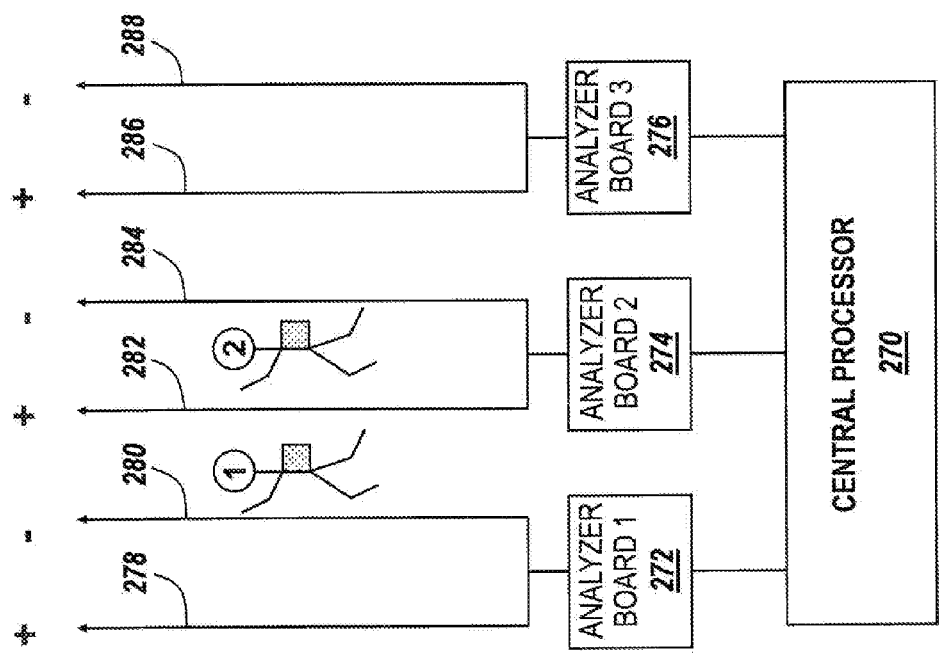

Prior to describing the wide area array in FIGS. 11 and 12, as to the basic system and referring now to FIG. 1, an individual 10 may be carrying on his or her person some contraband or explosives 12 which may for instance may be secreted in his or her underwear, or could even be surgically implanted. One such explosive is RDX and it is the purpose of the subject invention to be able to detect explosives in as little quantity as 75 grams which is approximately about a fifth of a cup. Terrorists and the like are using more and more sophisticated ways of secreting explosives and/or contraband and a physical examination of the individual may not yield the presence of such explosives or contraband. Not only may the explosives or contraband be surgically implanted in the individual, they may be swallowed in bags and be held internally in the gut until such time as their "removal".

Present systems for detecting such explosives or contraband such as back scatter X-rays are not effective to detect such secreted items and the use of higher power radiation is counterindicated for safety reasons.

On the other hand, as shown in FIG. 1, an explosive or contraband detection system 14 utilizes nuclear quadrupole resonance in which swept frequencies are applied to a balanced and terminated transmission line 16 embedded in a screening gate or housing 18 in which the elements of the balanced transmission line 20 and 21 as well as load 23 are embedded in the gate. The balanced transmission line has no frequency to which it is tuned, such that the application of signals for instance between 1.00 KHz and 10 MHz may be applied due to the non-tuned nature of the probe which is comprised of elements 20, 21 and 23.

As will be seen, the power necessary to detect nuclear quadrupole resonance is in general below 10 watts and often as little as 200 milliwatts, due to the subject explosives/contraband detection system which, inter alia, utilizes a directional coupler in the form of a circulator to cancel out the transmitted energy while receiving only the stimulated emission from the molecules in the target sample.

As used herein, the target sample 12 includes molecules having a particular recognizable spectrographic signature in which the spectral lines of the sample are recognizable when compared with the spectral lines generated through stimulated emission of all of the remaining molecules that surround the target sample.

For instance, glycine which is common in the human body has spectral lines that are distinguishable for instance from RDX spectral lines, with glycine in essence forming a background spectral signature which is to be distinguished.

While the subject invention will be discussed in terms of explosives, it is understood that the material under test may be molecules of any type having a known spectral signature. This includes contraband such as narcotics and other types of drugs such as heroin and cocaine which, due to the subject system in one embodiment involving stepped and swept frequency transmission enables one to eliminate the spectral signatures of non-target materials while being able to single out the spectra of target materials.

Figure 2:
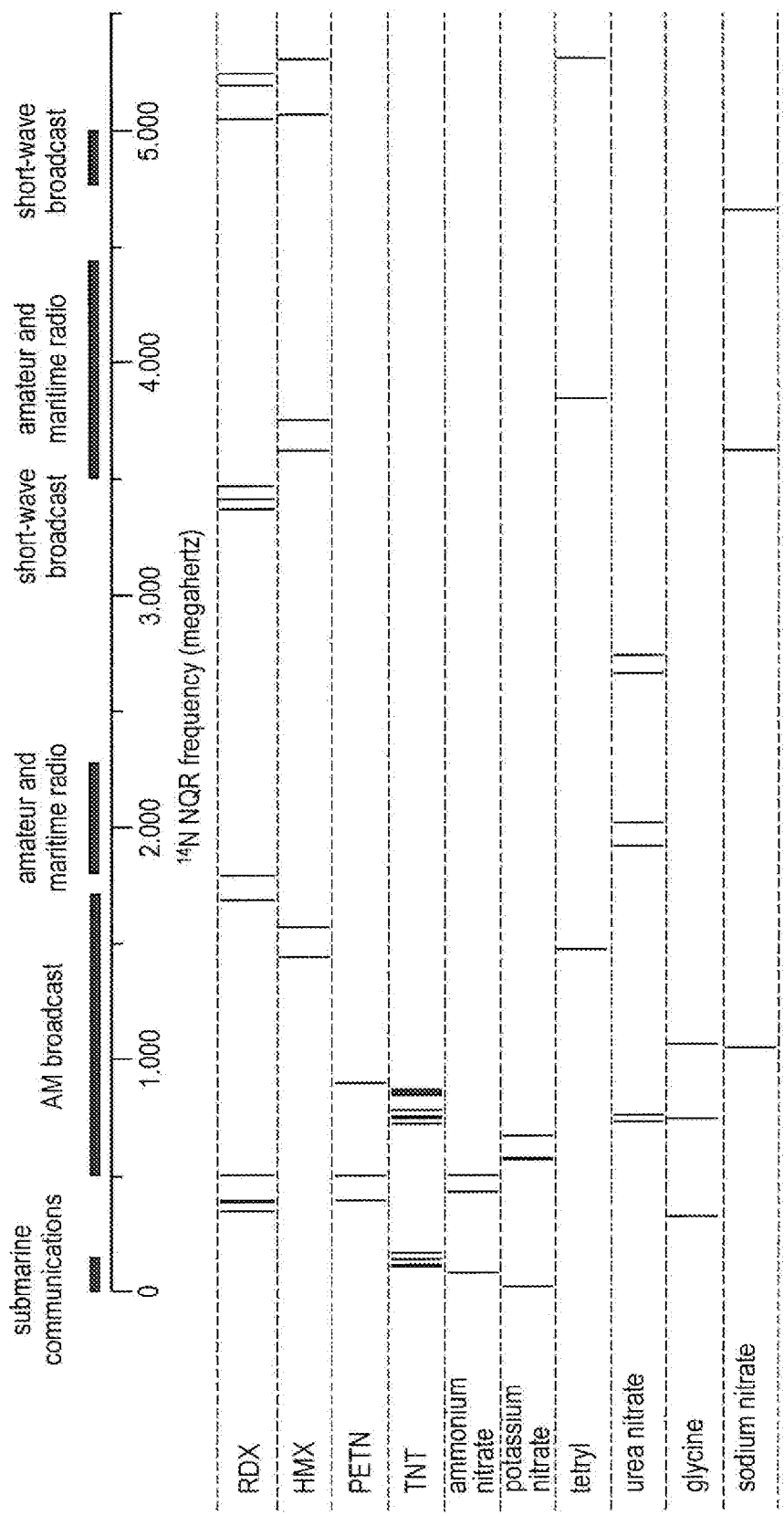
FIG. 2 is a graph showing the spectral signatures of a number of potential explosive materials indicating for RDX and HMX, a spectral signature in a 3-4 MHz range, with TNT indicating a spectral signature in the sub 1 MHz range as well as ammonium nitrate and potassium nitrate, with tetryl having a signature in the 3-4 MHz range and with urea nitrate having a spectral signature not only in the sub 1 MHz range but also in the 2-3 MHz range, noting that sodium nitrate has a very close spectral signature to one of the spectral lines of glycine.

Referring to FIG. 2, what is shown is a spectral chart for common explosive materials such as RDX, HMX, PETN, TNT, ammonium nitrate, potassium nitrate, tetral, urea nitrate and sodium nitrate, also as compared with the spectra of glycine.

What will be seen is that all of these materials have spectra between about 100 KHz and about 5 MHz, which spectra are detectable by the subject system. For instance, if one detects spectra of RDX in the 3-4 MHz band, this is clearly distinguishable from the glycine spectra which lie below 1.5 MHz.

Likewise one can distinguish PETN from RDX as well as being able to distinguish HMX from RDX due to the offset of the spectra of HMX in the 3-4 MHz band from the spectra of RDX.

Since the subject system detects stimulated emission from all of the molecules in the sample between the balanced transmission lines, it is possible through correlation processing to be able to provide a probability of a match between the spectral lines of the target material as opposed to the spectral lines due from molecules that are not target materials and which constitute background.

Figure 3:
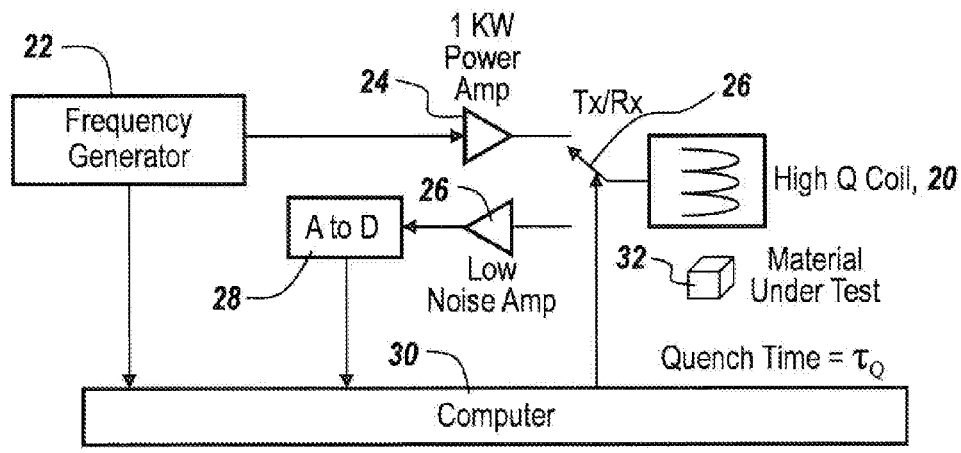
FIG. 3 is a diagrammatic illustration a prior art pulsed coil nuclear quadrupole resonance system illustrating the use of high power pulses and a high Q coil in which the system has a transmit-receive switch, the cycling of which depends on coil quench time.

Referring now to FIG. 3, what will be seen in the prior art pulsed coil nuclear quadrupole resonance system is the utilization of a high Q coil 20 which is driven from a frequency generator 22, the output of which is amplified by an amplifier 24 to the 1 kilowatt level. The signal from the amplifier is switched via a transmit/receive switch 26 and is applied to the coil during a pulsed sequence, with switch 26 being returned to the receive position at which point the high Q coil 20 is coupled to a low noise amplifier 26, to an analog-to-digital converter 28 and thence to a computer 30 for measuring the spontaneous emission response from material under test 32.

In short, since the system described in FIG. 3 measures the spontaneous emission of the material under test and since in order to generate enough spontaneous emission high power was deemed to be necessary, the system of FIG. 3 is clearly not usable around human beings for safety reasons.

Moreover, in order to be able to eliminate the effect of the transmitted power with respect to the relatively low power of the receive signal, it was necessary to be able to quench high Q coil 20 so as to be able to see the return from the material under test. The quench time, $\tau_Q$, is problematic with respect to providing realtime measurements. It has been found that it is important to be able to provide circuitry to be able to quench high Q coil 20 in order to increase the pulse repetition frequency. However, the quench time when utilizing a high Q coil is problematic as mentioned above.

Moreover, the utilization of a high Q coil is problematic because it also collects background, which background can oftentimes obscure the results.

Figure 4:
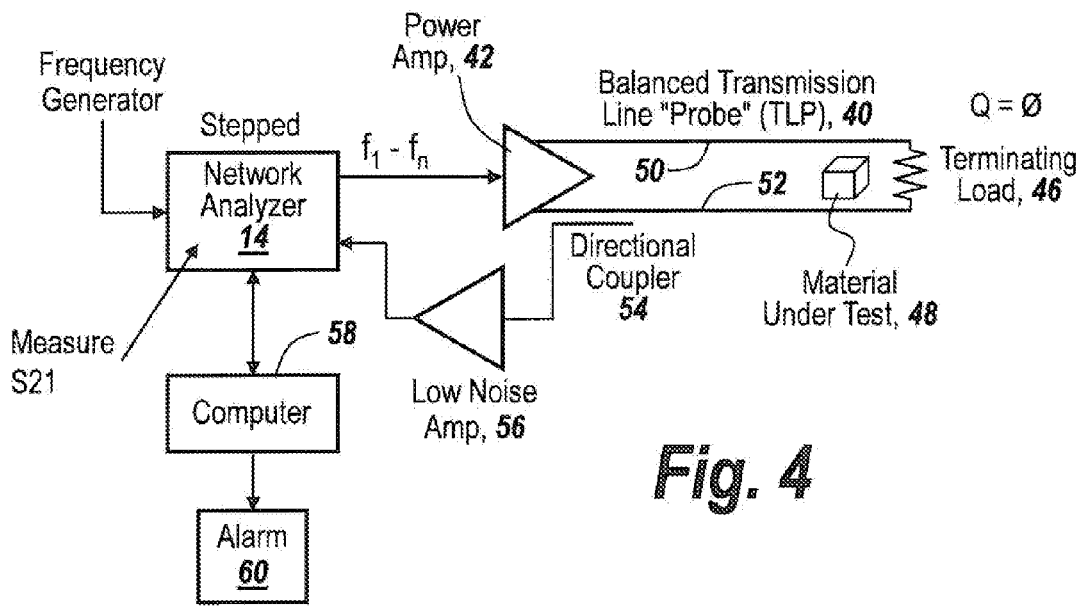
FIG. 4 is a diagrammatic illustration of the subject system illustrating a stepped network analyzer functioning as a frequency source for generating a number of stepped frequencies which are amplified by a low power amplifier to less than 10 watts in one embodiment, with the amplifier being coupled to a balanced transmission line probe in which the transmission line is terminated in a load and in which a directional coupler is utilized to detect the stimulated emission from a material under test, unimpeded by the output power applied to the transmission line.

On the other hand and referring now to FIG. 4, a balanced transmission line probe 40 is coupled to a power amplifier 42 which amplifies a frequency generator 44 output, in one embodiment provided by a stepped network analyzer. The transmission line is terminated by a terminating load 46.

When a material under test 48 is placed between the balanced transmission line elements 50 and 52, it has been found that the stimulated emission from the material under test can be sensed utilizing a directional coupler 54 coupled to a low noise amplifier 56 which is in turn coupled back to the network analyzer 44 that detects a S21 the very low level stimulated response of the material under test. It is noted that network analyzer 44 is coupled to a computer 58 such that the returned signal can be processed and an alarm 60 activated if the material under test has a spectral, signature match to that of a target material.

While it is possible to generate only one frequency corresponding to one the major spectral line of the target sample, it is useful to be able to scan frequencies for instance $f_1$-$f_n$ in order to detect the spectral lines of whatever materials might be between the elements of the balanced transmission line. Because the balanced transmission line has a Q of zero, not only is it possible to couple a wide frequency range of signals to the transmission line, the Q of zero also means that there is very little outside interference with respect to the signals that exist interior to the transmission line.

Moreover it has been found that while the flux densities vary at various positions between the transmission line elements, at least in the plane of the transmission line elements, locating a material under test above or below the plane of the transmission line elements does not materially affect the readings.

Figure 5:
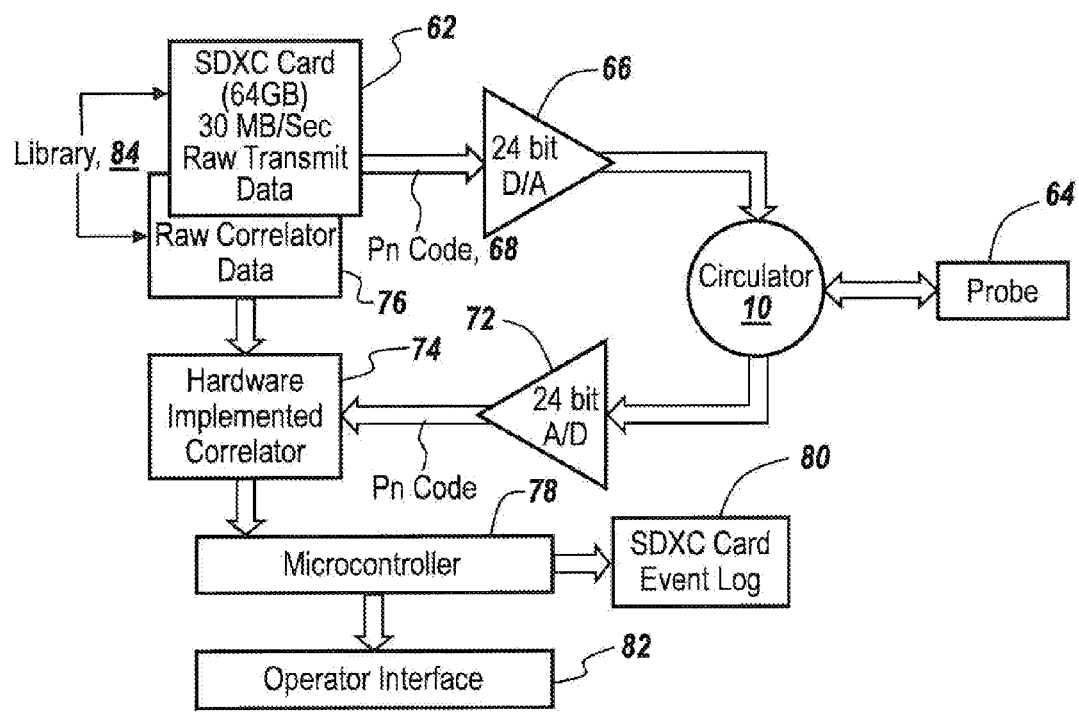
FIG. 5 is a block diagram of the subject system in which transmissions at various stepped frequencies are applied through a 24 bit digital-to-analog converter to a circulator that functions as a directional coupler, with the output of the circulator being converted by a 24 bit A-D converter to correlate the returns with raw correlated data from a library, the output of the hardware-implemented correlator provided to a microcontroller for detecting the existence of a particular material present at the probe; Note that this system can be used to test several simultaneous frequencies simultaneously.

Referring to FIG. 5, in one embodiment an memory card (such as a SXDX 62 gigabyte card) having a 30 MB per second transfer rate may be utilized to generate the 100 KHz to 10 MHz signals that are coupled to probe 64 utilizing a 24 bit digital-to-analog converter 66 to which is applied a PN code 68 in one embodiment.

The utilization of a pseudo-random code is for defeating jamming, with the pseudo-random code being similar to that utilized in GPS systems for this purpose.

The input to the probe and the output from the probe are coupled to a circulator 70 which, as described above, completely eliminates the effect of the transmitted, signal on the received signal, thereby to eliminate the problems of having to quench a high Q coil.

The output of circulator 70 is applied to a 24 bit analog-to-digital converter 72, with the receive PN code being applied to a hardware implemented correlator 74 that correlates the received stimulated emission information with raw correlator data 76 such that if there is a high correlation between the raw correlator data and the received data, microcontroller 78 may be used to drive memory card event log 80 and also provide an operator interface 82 alarm condition indicator.

Note that in terms of the generation of stepped frequency signals, a library 84 may be utilized that carries the spectral signatures of many types of target molecules. This results in the ability to generate a large variety of very narrow frequency signals which are applied to probe 64.

It will be appreciated that the frequency stability of the signal generator in the form of a network analyzer such as shown in FIG. 4 is critical due to the narrow nature of the spectral lines that are generated by the nuclear quadrupole resonance phenomena and the requirement of coherence.

Figure 6:
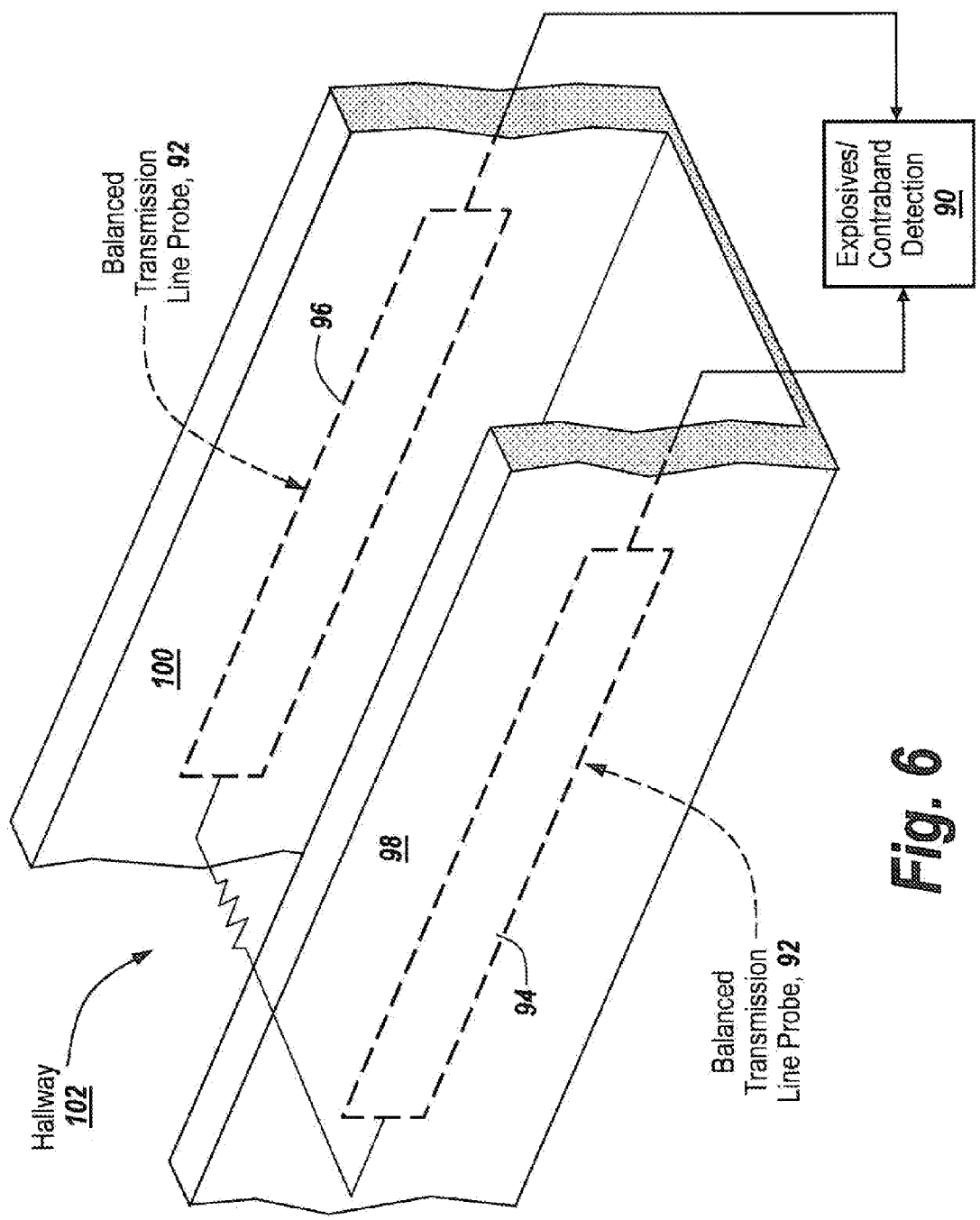
FIG. 6 is a diagrammatic illustration of an embodiment of the subject invention in which explosives detection includes the use of parallel foil strips on opposing walls of a hallway that function as a balanced transmission line probe for detecting target materials carried by a person walking down the hallway.

Referring now to FIG. 6, in one embodiment, an explosive contraband detection system 90 may be coupled to a balanced transmission line probe 92 which includes elements 94 and 96 embedded foil strips in hallway walls 98 and 100, with elements 94 and 96 terminated in a resistance load 102. In this case an entire hallway may be monitored for the presence of target molecules whether carried by a person or in some other conveyance as it transits down a hallway.

Figure 7:
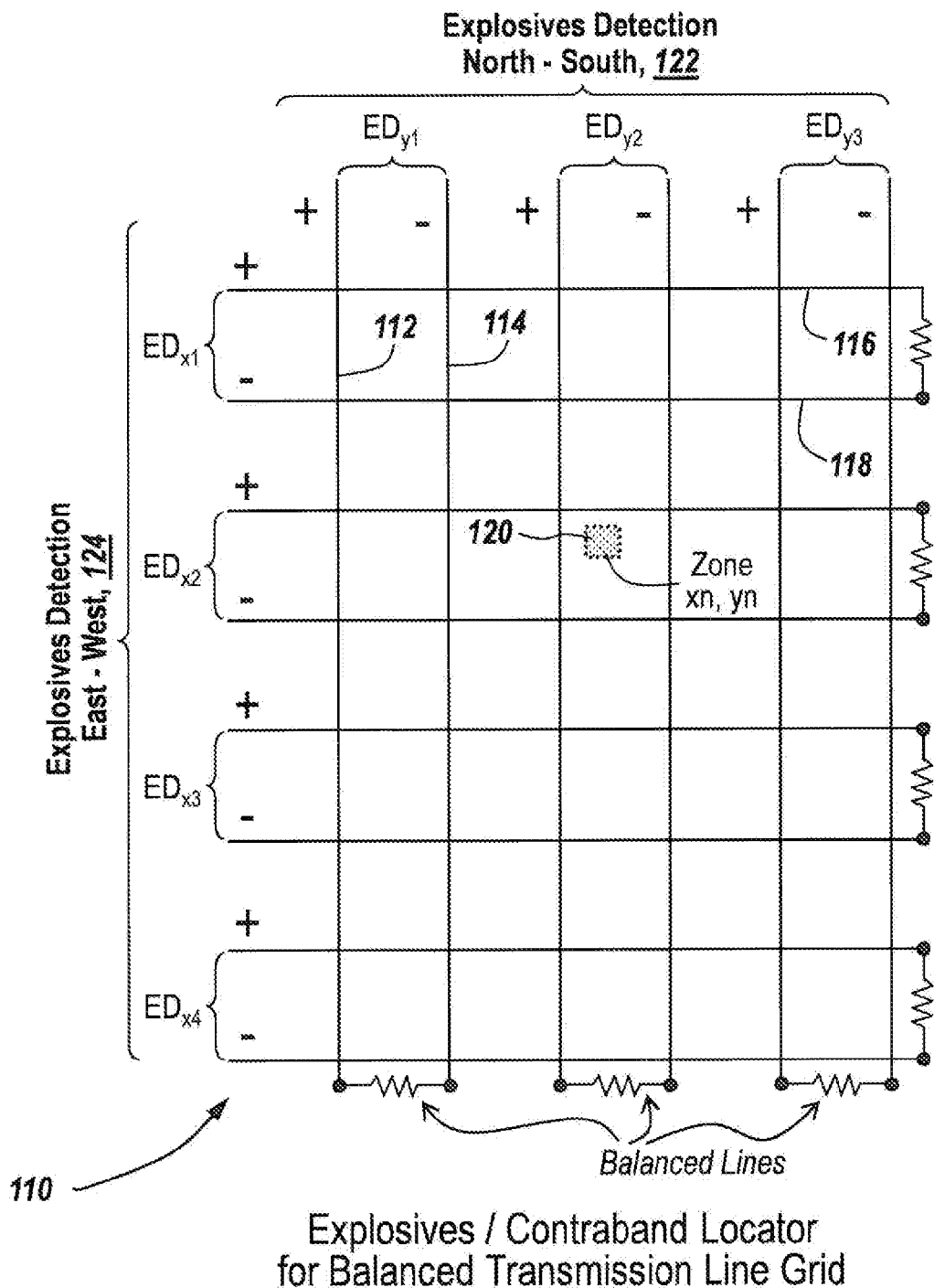
FIG. 7 is a diagrammatic illustration of the utilization of a grid of balanced transmission lines for the location of a target material carried for instance by an individual who traverses the grid.

Referring to FIG. 7, it is possible to provide a grid of balanced transmission lines here shown at 110 to include pairs of transmission lines for instance vertical pairs 112 and 114 indicated by the plus and minus nomenclature for the particular transmission line. Likewise, a crossing or transverse transmission line structure may include transmission lines 116 and 118. By monitoring the results on the various transmission lines one can localize the target molecule as illustrated at 120 as being at position $x_n$, $y_m$. This kind of grid, whether on the floor or surrounding a building can track the presence of explosives or contraband materials and therefore determine the track or path of the individual or conveyance which is transporting these materials.

For this particular embodiment the detection of explosives in for instance the north/south direction here illustrated at 122 is correlated with at explosive detection in east/west direction here illustrated at 124 to provide location.

The Wide Area Array

Considering for instance that a terminated balanced line contains two elements, one element is called a plus element and the other is called a minus element. The magnetic flux lines are in a plane perpendicular to the axis of the elements. In one configuration, a large area can be covered using a number of side-by-side plus/minus lines. For instance, these lines could be laid out in a carpet at an airport to track people carrying explosives on their person. Thus, one can monitor the transmission lines to be able to tell where someone carrying explosives is walking and to be able to track their path.

More particularly and referring now to FIGS. 11 and 12, in order to be able to provide coverage over a wide area, to geolocate a sensed substance, for instance carried by individuals 202 and 204, a blanket array, wide area, detection grid 206 stretches across an area 208 for instance in front of a building 210 having an ingress 212.

When the subject system is utilized to protect an area from intrusion especially by those carrying explosives, the wide area blanket array detection system includes balanced transmission line plus/minus pairs 212 in spaced adjacently one to the other running horizontally as illustrated, whereas a crossed set of balanced transmission line pairs 214 overlays the balanced transmission line pairs 212 so as to form the aforementioned grid.

In the horizontal direction and as mentioned before, a stepped network analyzer measuring board 220 includes a stepped network analyzer 222 coupled to an amplifier 224 which provides a balanced output 226 and 228 to a horizontally running balanced transmission line comprised of plus/minus lines 230 and 234. A directional coupler 236, coupled to a low noise amplifier 238 is connected as an input to the stepped network analyzer which measures S21 in a particular horizontal direction, here shown by $Y_m$.

For the vertical direction, a network analyzer board 240 includes a stepped network analyzer 242 coupled to an amplifier 244 having a balanced output 246 and 248 coupled to balanced transmission line elements 250 and 252. Here a directional coupler 254 is coupled to a low noise amplifier 256, which provides a signal coupled back to stepped network analyzer 242 such that $S21_{xn}$ is measured.

The above establishes a cross point array or grid with each of the balanced transmission lines is terminated by a resistor 258.

Assuming that the stepped network analyzers are coupled to a localization computer 260, its output provides the cross point location on the grid.

As will be discussed, if a grid type of balanced transmission line array is not used, then the sensed substance can be located by detecting the phase between the transmitted and the received signal associated with a balanced transmission line, thereby to place the sensed substance at a calculated distance from the balanced line feedpoint.

In operation, the network analyzer board sends a swept CW signal down a balanced transmission line. If sensed substances such as explosives are present, a stimulated emission is picked up by the directional coupler. S21 is continuously measured and compared to an S21 sweep in memory, taken where no substances or objects are inside the transmission lines. The phase of the S21 output depends upon the distance of the detected substance from the fed end of the transmission line. This provides information about the location of the sensed substances or explosives.

It is noted that the network analyzer board houses a power amplifier.

For each of the balanced transmission lines in the horizontal directional and each of the balanced transmission lines in the vertical direction, there is a separate network analyzer board coupled to the respective balanced transmission lines. These boards simultaneously transmit the CW signals down the balanced transmission lines, with each of the lines carrying CW signals of identical frequency and, in one embodiment, zero phase difference between the signals.

Thus, each of the balanced transmission lines in the horizontal and the vertical direction are simultaneously fed with signals having identical frequencies. Moreover, the signals coupled to the balanced transmission lines are in phase. As a result, if there is a sensed substance in between the lines of the balanced transmission line then there will be an S21 signal indicative of the substance.

Note, network analyzer board 220 is duplicated as illustrated at 220' whereas network analyzer 240 is duplicated as illustrated by network analyzer board 240'. Any significant difference between the S21 measurement with the S21 values in memory provides an indication of a sensed substance, in one embodiment, in a crossed point detection system.

Referring to FIG. 12, it can be seen that a central processor 270 controls analyzer boards 272, 274 and 276 coupled respectively to balanced transmission lines 278-280, 282-284 and 286-288.

As mentioned with respect to FIG. 11, all transmission lines are fed in-phase. It is noted that the measured S21 information from each analyzer board is routed to a central processor.

If for instance a Perpetrator 2 is located between transmission lines 282 and 284, Perpetrator 2 will be detected by analyzer board 2.

If however Perpetrator 1 is between the balanced transmission lines 278-280 and 282-284, then Perpetrator 1 will be seen by both analyzer board 1 and analyzer board 2.

The ratios of the signature reflection from analyzer board 1 and analyzer board 2 is a function of exactly where Perpetrator 1 is located.

It will be seen that using the ratios and the phases of the signature reflections it is possible to track perpetrators as they progress along the floor or across the array of balanced transmission lines.

It will also be noted that in one embodiment, the analyzer boards are controlled to provide a common sweep by central processor 270.

Figure 8:
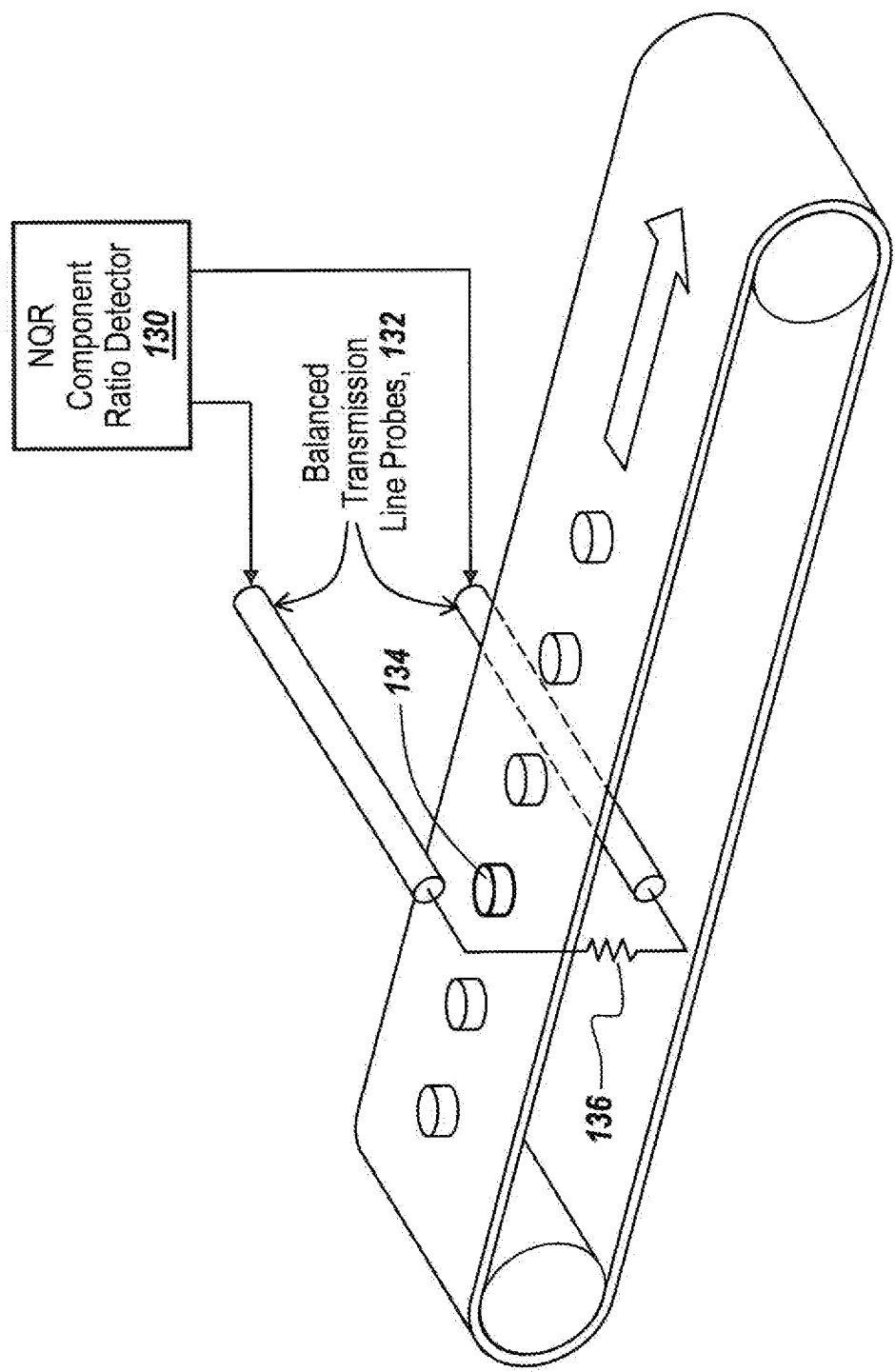
FIG. 8 is a diagrammatic illustration of the use of the subject system as a nuclear quadrupole resonance component ratio detector for detecting the ratio of molecular components in material proceeding down a production line to detect component ratios in a non-destructive environment on the fly as the material passes between the balanced transmission line probe elements.

Referring now to FIG. 8, one of the important characteristics of the subject system is that the molecular component ratio can be detected on the fly in a production line environment to provide non-destructive testing. Here a nuclear quadrupole resonance component ratio detector 130 is utilized with a balanced transmission line probe 132 to, for instance, detect the molecular composition of a drug 134 in pill form as the pills pass through the balanced transmission line probe. It has been found that by sweeping the frequency of the signals to the balanced transmission line probe one can detect not only the spectral lines of the various components in question, but also can detect the ratio of the target components.

Thus, rather than having to perform destructive tests in order to ascertain the constituents of a product being manufactured, one can non-destructively detect the component ratios utilizing the subject nuclear quadrupole resonance system.

Figure 9:
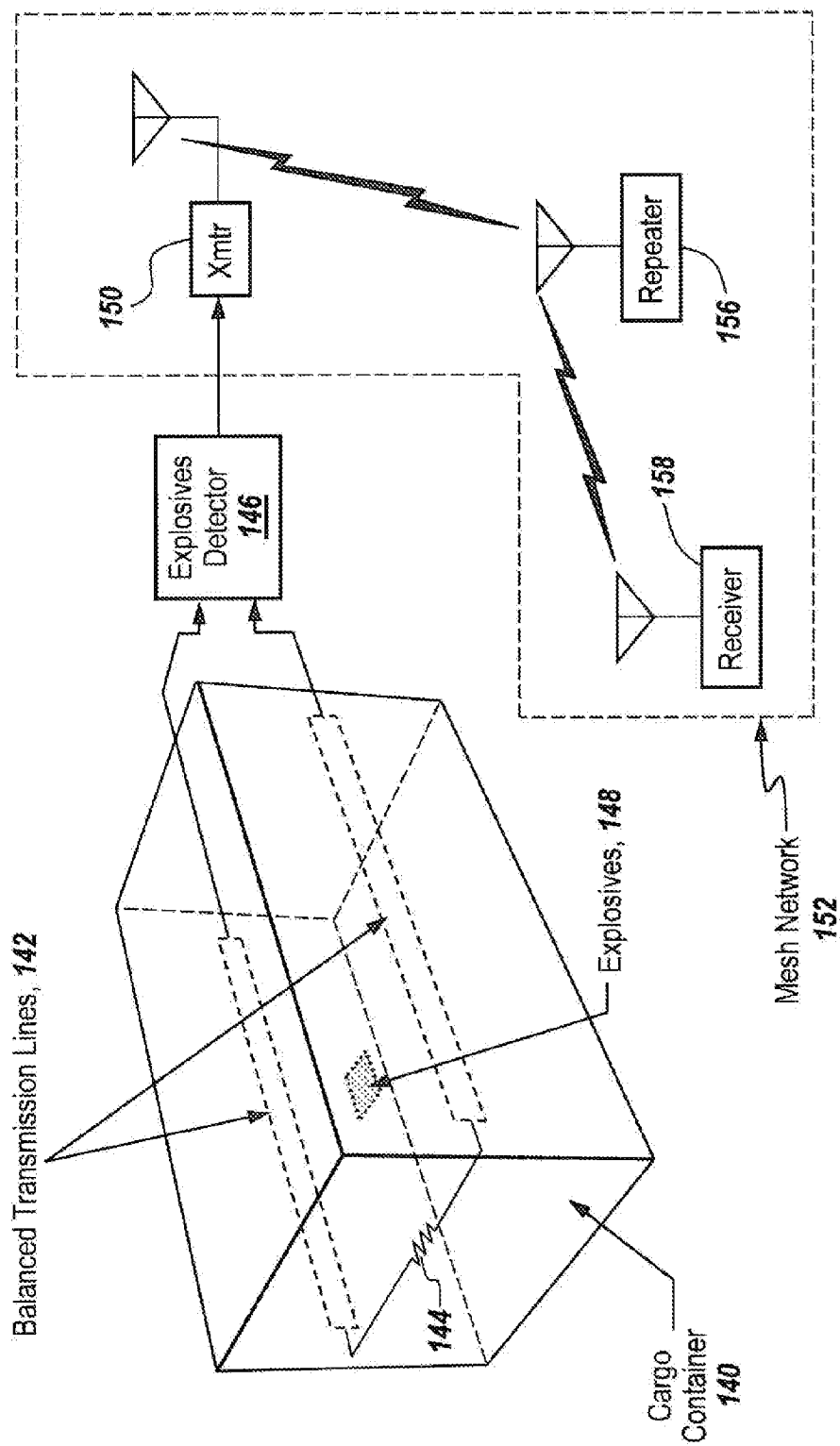
FIG. 9 is a diagrammatic illustration of a shipboard container inspection system utilizing the subject system in combination with a mesh radio network to report incidents to a cargo control room.

Referring now to FIG. 9, another embodiment of the subject system is the ability to track the contents of cargo containers that may either be placed shipboard or on other modes of conveyance in which, as illustrated, a cargo container 140 may be provided with internal balanced transmission lines 142 terminated as illustrated at 144 and coupled, for instance, to an explosive detection system 146 of the subject nuclear quadrupole resonance variety. If for instance the containers contain explosives or contraband, here illustrated at 148, whether these materials are initially placed in the container or later clandestinely placed into a sealed container, their presence can be detected as illustrated at 146 by an explosives detector. Through the use of a mesh network 148, the detected results can be communicated from explosives detector 146 and a co-located transmitter 150 which is part of a self establishing mesh network 152 aboard a ship to the cargo control room. Mesh network 152 includes one or more repeaters 156 which relays the information from transmitter 150 to a receiver 158 in the cargo control room.

It is noted that when monitoring containers, due to the length of time on board ship, the integration times available for the sensing of the stimulated emissions are dramatically increased. This long integration time can accommodate lower power detection. What this means is that an exceedingly robust system is available for detecting the relatively minute simulated emissions, with integrating occurring over a long period of time, thanks to the fact that the containers are in transit for substantial periods of time. While this embodiment of the subject system has been described in terms of shipboard containers, any kind of container monitoring on conveyances is within the scope of the subject invention.

It is also possible for instance to utilize the subject system to detect contraband or explosives in trucks that pass through a portal. This is possible due to the relatively thick skin depths associated with metal containers that permit penetration of low frequency signals so that the transmission line carried signals can penetrate well into the containers. Thus, the subject system may be utilized to detect not only person-carried contraband and explosives, but also truck or vehicle-carried contraband or explosives, as for instance they proceed through a portal or checkpoint.

Figure 10:
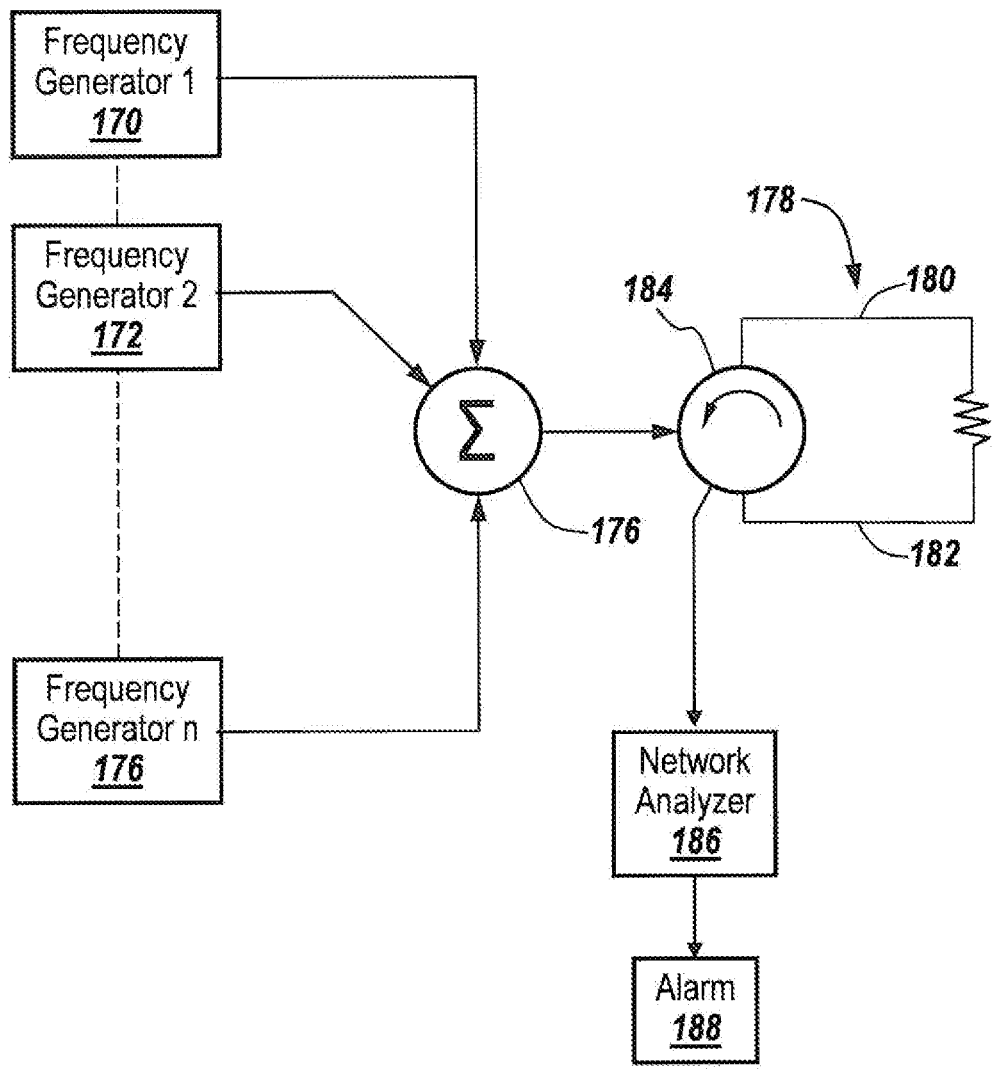
FIG. 10 is a block diagram of parallel-connected frequency generators coupled to a terminated balanced transmission line.

Referring now to FIG. 10, while the subject system has been described in terms of stepped frequency production, it is possible to use a parallel-connected set of frequency generators 170, 172 and 174, the outputs of which are summed at 176 and applied to a balanced transmission line 178 having elements 180 and 182 through a circulator 184. It is also possible to synthesize multi frequency signals digitally. The output of circulator 184 is applied to a network analyzer or receiver 186 that, inter alia, enables correlations between spectral lines found at the various frequencies to target molecule spectral lines, whereupon signals representative of the presence of the target molecule may be applied to an alarm 188.

Thus, whether or not stepped frequencies are utilized, or whether a number of parallel-connected frequency sources are utilized, spectral lines of target and non-target molecules can be quickly scanned.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A system for detecting substances utilizing nuclear quadrupole resonance across an extended area, comprising:
    an array of balanced transmission lines located side by side in an area, wherein each balanced transmission line is terminated with a load equal to the impedance of the transmission line so that the transmission line is balanced and effectively has a Q of zero;
    a frequency source for simultaneously driving each of said transmission lines with a transmission signal having a frequency equal to that of a spectral line of a substance located in the area;
    a series of detectors, one each per balanced transmission line, configured to detect received signals from said balanced transmission lines indicative of stimulated emissions caused by nuclear quadrupole resonance of the substance near said balanced transmission lines; and,
    a processor coupled to said detectors for processing any detected received signals to indicate the presence of said substance in said area.

2. The system of claim 1, wherein said frequency source includes a network analyzer.

3. The system of claim 2, wherein one network analyzer is provided per balanced transmission line, the network analyzers being activated to generate a signal to be coupled to an associated balanced transmission line.

4. The system of claim 3, wherein said network analyzer couples a CW transmission signal to an associated balanced transmission line.

5. The system of claim 4, wherein said CW transmission signals are in-phase.

6. The system of claim 1, wherein said detector includes a directional coupler coupled to a balanced transmission line to isolate the received signal from the transmission signal so that interference between the transmitted signal and the received signal will be minimized.

7. The system of claim 1, wherein said detector includes a number of separate network analyzers each having an output coupled to a different balanced transmission line and each having an input from the balanced transmission line to which it is coupled.

8. The system of claim 7, wherein each of said network analyzers outputs a complex ratio between the signals coupled to an associated balanced transmission line and the received signal from the associated balanced transmission line.

9. The system of claim 1, wherein said array includes a grid of a first set of terminated balanced transmission lines overlaid in a normal orientation with a second set of terminated balanced transmission lines.

10. The system of claim 9, and further including a computational element coupled to said series of detectors for determining from the output thereof the location of a sensed substance in said area.

* * * * *